(12) United States Patent
GuÐmundsdóttir et al.

(10) Patent No.: US 11,338,021 B2
(45) Date of Patent: May 24, 2022

(54) COMBINATION THERAPIES

(71) Applicant: ENZYMATICA AB, Lund (SE)

(72) Inventors: Ágústa GuÐmundsdóttir, Reykjavik (IS); Reynir Scheving, Kopavogur (IS)

(73) Assignee: ENZYMATICA AB, Lund (SE)

( * ) Notice: Subject to any disclaimer, the term of this patent is extended or adjusted under 35 U.S.C. 154(b) by 412 days.

(21) Appl. No.: 15/746,888

(22) PCT Filed: Jul. 22, 2016

(86) PCT No.: PCT/EP2016/067570
§ 371 (c)(1),
(2) Date: Jan. 23, 2018

(87) PCT Pub. No.: WO2017/017027
PCT Pub. Date: Feb. 2, 2017

(65) Prior Publication Data
US 2020/0085921 A1    Mar. 19, 2020

(30) Foreign Application Priority Data

Jul. 24, 2015   (EP) .................... 15178209

(51) Int. Cl.
| | | |
|---|---|---|
| *A61K 38/48* | (2006.01) | |
| *A01N 63/50* | (2020.01) | |
| *A61P 31/04* | (2006.01) | |
| *A61K 9/00* | (2006.01) | |
| *A61K 45/06* | (2006.01) | |

(52) U.S. Cl.
CPC .......... *A61K 38/4826* (2013.01); *A01N 63/50* (2020.01); *A61K 9/0043* (2013.01); *A61K 9/0053* (2013.01); *A61K 45/06* (2013.01); *A61P 31/04* (2018.01)

(58) Field of Classification Search
CPC .. A61K 38/4826; A61K 45/06; A61K 9/0043; A61K 9/00053; A01N 63/50
See application file for complete search history.

(56) References Cited

U.S. PATENT DOCUMENTS

| | | | |
|---|---|---|---|
| 4,235,871 A | 11/1980 | Papahadjopoulos et al. | |
| 5,851,451 A | 12/1998 | Takechi et al. | |
| 2002/0037260 A1* | 3/2002 | Budny ................. | A61K 31/545 424/49 |
| 2002/0141987 A1 | 10/2002 | Bjarnason | |
| 2011/0129454 A1 | 6/2011 | Olmstead | |
| 2014/0221610 A1 | 8/2014 | Zlotkin | |
| 2014/0377192 A1* | 12/2014 | Schaeffer-Korbylo ..................... | A61K 8/66 424/50 |

FOREIGN PATENT DOCUMENTS

| | | |
|---|---|---|
| CN | 103007258 A | 4/2013 |
| CN | 103191491 | 7/2013 |
| CN | 104602700 | 5/2015 |
| EP | 0 213 303 A2 | 11/1987 |
| EP | 1 202 743 B1 | 10/2004 |
| JP | 2003/502071 | 1/2003 |
| JP | 2013/511555 | 4/2013 |
| JP | 2014/520098 | 8/2014 |
| WO | WO 00/78332 A2 | 12/2000 |
| WO | WO-2013095439 A1 * | 6/2013 ............... A61K 8/66 |
| WO | WO 2013/170022 | 11/2013 |
| WO | WO 2013/170128 | 11/2013 |
| WO | WO 2015/114343 A1 | 8/2015 |
| WO | WO 2015/150799 A1 | 10/2015 |

OTHER PUBLICATIONS

Gudmundsdóttir et al. "Isolation and characterization of cDNAs from Atlantic cod encoding two different forms of trypsinogen", European Journal of Biochemistry, 217, 1091-1097, 1993 (Year: 1993).*
Search Result 1, May 11, 2021 (Year: 2021).*
Ásgeirsson et al., "Purification and characterization of trypsin from the poikilotherm *Gadus morhua*," 1989, *Eur. J. Biochem.* 180:85-94.
Ásgeirsson & Bjarnason, "Structural and Kinetic Properties of Chymotrypsin from Atlantic Cod (*Gadus morhua*). Comparison with Bovine Chymotrypsin," 1991, *Comp. Biochem. Physiol.* vol. 99B, No. 2, pp. 327-335.
Augustin, "Assessment of Enzymatic Cleaning Agents and Disinfectants Against Bacterial Biofilms", (Jan. 1, 2004), Journal of Pharmacy and Pharmaceutical Sciences, v. 7(1), pp. 55-64, URL: https://helda.helsinki.fi/handle/1975/547.
Bals et al: "Human-Beta-Defensin 2 is a Salt-sensitive Peptide Antibiotic Expressed in Human Lung", J. Clin. Invest, (Sep. 1, 1998), vol. 102, No. 5, pp. 874-880.
Banar et al. "Evaluation of Mannosidase and Trypsin Enzymes Effects on Biofilm Production of *Pseudomonas aeruginosa* Isolated from BurnWound Infections," PLoS One, 2016, 11(10) e0164622.
Darouiche et al: "Antimicrobial and Antibiofilm Efficacy of Triclosan and DispersinB® Combination", Journal of Antimicrobial Chemotherapy, 2009, 64, 88-93.
GenBank Accession No. ACO90397, Jul. 24, 2016.
GenBank Accession No. CAA55242.1, Jun. 27, 2018.
Gudmundsdóttir et al, "Potential Use of Atlantic Cod Trypsin in Biomedicine" Biomed Research International, (Jan. 1, 2013), vol. 54, No. 8, doi:10.1097/WON.0b013e3181bfdf83, ISSN 2314-6133, pp. 16-11.
Huang and Miller, "*A Time-Efficient, Linear-Space Local Similarity Algorithm,*" *Adv. Appl. Math.* (1991) 12:337-357.
Iwase et al: "*Staphylococcus epidermidis* Esp inhibits *Staphylococcus aureus* biofilm formation and nasal colonization", Nature, (May 20, 2010), vol. 465, No. 7296, doi:10.1038/nature09074, ISSN 0028-0836, pp. 346-349.

(Continued)

*Primary Examiner* — Ruth A Davis
(74) *Attorney, Agent, or Firm* — Parker Highlander PLLC

(57) ABSTRACT

The invention provides combination therapy for use in treating a bacterial biofilm in a subject comprising (a) a polypeptide having serine protease activity and (b) one or more antibiotic compounds. Also provided are compositions and methods of use of the same.

14 Claims, 8 Drawing Sheets

Figure 1:
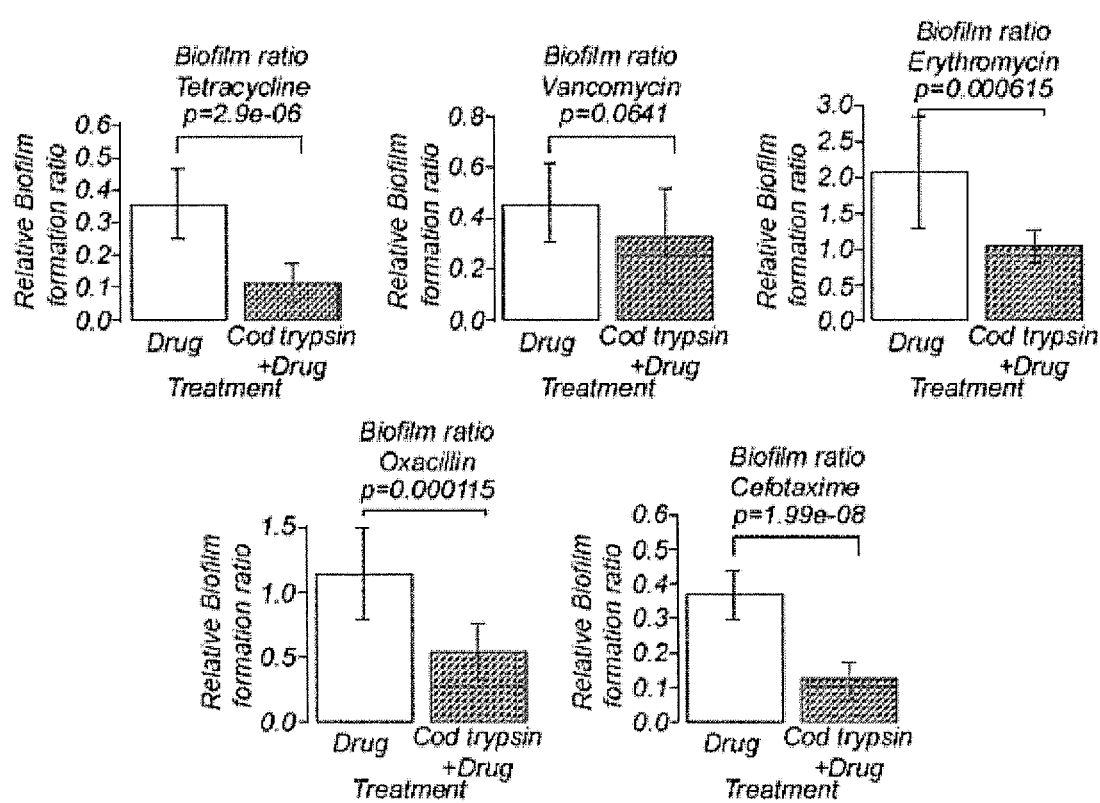

Specification includes a Sequence Listing.

(56) References Cited

OTHER PUBLICATIONS

Moon et al., "Isolation and Characterization of a Highly Specific Serine Endopeptidase from an Oral Strain of *Staphylococcus epidermidis*," Biol. Chem, vol. 382, pp. 1095-1099, Jul. 2001.
NIH Guides "Research on microbial biofilms (PA-03-047)", NIH, National Heart, Lung, and Blood Institute, Dec. 20, 2002.
Pozo & Patel, 2007, "The Challenge of Treating Biofilm-associated Bacterial Infections," *Clin. Pharmacol. Ther.* vol. 82, No. 2, 204-9.
Rogers et al., "Synergistic Effects between Conventional Antibiotics and 2-Aminoimidazole-Derived Antibiofilm Agents," AntiMicrobial Agents and Chemotherapy, May 2010, p. 2112-2118.
Sigma-Aldrich, Trypsin Serine Protease Enzyme, https://www.sigmaaldrich.com/technical-documents/articles/biology/tryspin.printerview.html, pp. 1-4.
Stefansson, B., L. Helgadottir, S. Olafsdottir, A. Gudmundsdottir, and J. B. Bjarnason, 2010, Characterization of cold-adapted Atlantic cod (*Gadus morhua*) trypsin I—Kinetic parameters, autolysis and thermal stability: Comparative Biochemistry and Physiology B—Biochemistiy & Molecular Biology, v. 155, p. 186-194.
Stewart & Costerton, "Antibiotic Resistance of Bacteria in Biofilms," 2001, *Lancet*, vol. 358, 135-8.
Tets et al., "Impact of Exogenic Proteolytic Enzymes on Bacteria," 2004, Academician, vol. 49, No. 12.
Thompson et al., "CLUSTAL W: improving the sensitivity of progressive multiple sequence alignment through sequence weighting, position-specific gap penalties and weight matrix choice," 1994, *Nucl. Acid Res.* vol. 22, No. 22, 4673-4680.
Dr. Willip, "Natural Anti-Biofilm Agents," The Science of Nutrition, Mar. 13, 2015, pp. 1-23.
Wobenzym® patient information leaflet, 6636/07, 2017.
CN 103191491, English Machine Translation, dated May 1, 2021.
GenBank, Accession: CAA54214.1, "Trypsinogen I [Gadus morhua]", dated Apr. 18, 2005, downloaded from www.ncbi.nlm.nih.gov/protein/CAA54214.1 on Dec. 9, 2020.
Artini, M., et al. "Comparison of the action of different proteases on virulence properties related to the staphylococcal surface." *Journal of applied microbiology* 114.1 (2013): 266-277.
Ying Wang et al., Drug efficacy analysis and clinical practice, China Medical Science Press, p. 237, 2008. English Machine Translation.
Ying Wang et al., Drug efficacy analysis and clinical practice, China Medical Science Press, p. 237, 2008.
Wenfu Zhang et al., "New Technology and Application of Modern Disinfection," Military Medical Science Press, p. 109, Jul. 31, 2013. English translation appended.
Office Communication issued in CN 201680042973.9, dated Jan. 12, 2022. English translation appended.

\* cited by examiner

COMBINATION THERAPIES

This application is a national phase application under 35 U.S.C. § 371 of International Application No. PCT/EP2016/067570, filed Jul. 22, 2016, which claims priority to European Patent Application No. 15178209.1, filed Jul. 24, 2015. The entire text of each of the above referenced disclosures is specifically incorporated herein by reference.

FIELD OF THE INVENTION

The present invention relates to combination therapies for the treatment and prevention of bacterial biofilms, such as those present in recurrent upper and lower respiratory tract infections.

BACKGROUND OF THE INVENTION

Biofilms are heterogeneous, complex 3D matrices that comprise a population of microbial cells embedded in an extracellular matrix (ECM). They are not just a passive assembly of cells, but are structurally and dynamically complex biological systems that form local ecosystems. The microbial cells within a biofilm population appear to co-operate and take on special functions. By co-operating and forming a protective ECM, the biofilm provides the microorganisms with a protected mode of growth that allows them to colonise diverse environments. The biofilm mode of growth allows the bacteria to counteract the immune system of the host as well as antibiotics and similar bacteriostatic and bactericidal agents.

The development of biofilm thus allows a population bacteria to show resistance to antibiotics. Bacteria growing in biofilms are more difficult to defeat than their planktonic, i.e. free-living, counterparts (see del Pozo & Patel, 2007, Clin. Pharmacol. Ther. 82:204-9 and Stewart & Costerton, 2001, Lancet 358:135-8).

Biofilms can consist of mono or poly-bacterial populations adhering to virtually any biological or non-biological surface. In such multicellular populations, cells adhere to each other. A majority of bacterial species, as well as archaea, protozoa, fungi and algae, have the ability to adhere to surfaces and to each other and form biofilm structures. Formation of biofilms typically begins with the attachment of free-floating microorganisms to a surface. When the expressions of numerous genes are changed, a planktonic cell undergoes a phenotypic shift and switches from the free living mode to the biofilm mode of growth. The first colonists adhere to the surface initially through weak, reversible adhesion, which may become stronger by production of cell adhesion structures such as pili. Once colonization has begun, the biofilm grows through a combination of cell division and appearance and binding of new bacteria. The first colonists facilitate the arrival of other cells by providing more diverse adhesion sites and by beginning to build the matrix that holds the biofilm together.

Biofilms may form in a variety of settings, such as in nature, domestic industrial and hospital settings, where they exert various effects which may be positive or negative depending on the context.

In the medical setting, biofilms form persistent reservoirs of bacteria on surfaces. Biofilms can occur both directly on a patient and indirectly on surfaces of the patient's immediate environment. Biofilms that are present directly on a patient are commonly associated with recurrent infections, while the transfer of bacteria from the immediate environment to the patient is implicated in both primary and recurrent infections. Examples of biofilm in hospital settings are biofilms on catheters and other forms of tubing, and on implants such as heart valves and joint prosthesis.

In the industrial settings biofilms can be both essential and detrimental. For example, in recent developments of efficient microbial bioreactors, biofilm colonised electrodes are used to generate electricity. Biofilms have also been explored as possible biological factories of compounds, e.g. cellulose.

International patent application WO 00/78332 provides use of fish serine proteases including trypsins and chymotrypsin derived from cod such as Atlantic cod for treating and/or preventing a variety of diseases and disorders. These are for example inflammatory diseases, infectious diseases caused by viruses, bacteria and fungal species and diseases where a receptor binding mechanism is involved in the pathogenesis.

Augustin et al. (2004) and Gudmundsdottir et al. (2013) discuss the possibility of using enzymes to remove biofilms. The use of enzymes alone however is not sufficient to destroy the bacteria and they can, given time and the appropriate environment, reattach themselves to the surface or any nearby surface and rebuild the biofilm (Augustin et al., 2004; Gudmundsdottir et al., 2013).

Trypsin from cod has been shown to facilitate removal of dead skin by debridement and thereby aids in the normal skin repair process. The main problem of using hydrophilic marine enzymes, like cod trypsin and other serine proteases from cold environments, is that such enzymes are sensitive to inactivation by heat and are therefore relatively unstable at room temperature (Stefansson et al., 2010). The use of cod trypsin in cosmetics, medical devices and pharmaceuticals is dependent on increasing the stability of the enzyme.

Biofilms have been found to be involved in a wide variety of microbial infections in the body, by one estimate 80% of all infections (see "Research on microbial biofilms (PA-03-047)", NIH, National Heart, Lung, and Blood Institute, 2002-12-20). Infectious processes in which biofilms have been implicated include common problems such as urinary tract infections, catheter infections, middle-ear infections, coating contact lenses, and less common but more lethal processes such as endocarditis, infections in cystic fibrosis, and infections of permanent indwelling devices such as joint prostheses and heart valves.

Interestingly, microorganisms such as bacteria that attach to a surface and grow as a biofilm are less vulnerable to conventional antibiotic treatments. Reduced antibiotic susceptibility contributes to the persistence of biofilm infections such as those associated with implanted devices. The protective mechanisms at work in biofilms appear to be distinct from those that are responsible for conventional antibiotic resistance. In biofilms, poor antibiotic penetration, nutrient limitation, slow growth, adaptive stress responses, and formation of persister cells are hypothesized to constitute a multi-layered defence.

Furthermore, biofilm cultures are typically highly refractory to eradication with chemotherapy, without developing genotypic resistance. Consequently, the number of therapeutic options is limited and the development of novel antimicrobial agents with antibiofilm activity is increasingly important.

Hence, there is a need for new methods of killing, inhibiting or preventing the growth of a bacterial biofilms (both in medical and non-medical environments).

SUMMARY OF THE INVENTION

A first aspect of the invention provides a combination therapy for use in treating a bacterial biofilm in a subject comprising (a) a polypeptide having serine protease activity and (b) one or more antibiotic compounds.

By "combination therapy" we include any form of concurrent or parallel treatment with the two or more therapeutic agents. Thus, such therapies include the separate administration of the polypeptide and antibiotic compounds, as well as the provision of a single composition comprising both therapeutic agents mixed together.

By "treatment" we include both therapeutic and prophylactic use of the combined therapeutic agents. In relation to therapeutic use, it will be appreciated by persons skilled in the art that the combination therapy may completely eradicate an existing bacterial biofilm or it may provide a partial benefit (such as a reduction in the size of the bacterial population constituting the biofilm and/or slowing of growth of the bacterial population constituting the biofilm). Likewise, in relation to prophylactic use, the combination therapy may completely prevent biofilm formation or may provide only a partial benefit, such as reducing the likelihood and/or severity of infection with a bacterial biofilm.

In one embodiment, the subject is human. However, the combination therapies of the invention may also be useful in a veterinary setting, for example in the treatment of bacterial biofilms in domestic and/or farm animals (including dogs, cats, horses, cattle, pigs, sheep and the like).

Individually, antibiotics and serine proteases (such as trypsins) are not capable of resolving biofilm infections. Although antibiotics can be used to treat systemic and local bacterial infections with varying degrees of success, such compounds cannot readily penetrate the extracellular matrix of biofilms and so have limited efficacy in killing bacteria within biofilms. Antibiotics are therefore unable to completely resolve infections originating from biofilms.

Serine proteases (such as trypsins) can dissolve the extra cellular matrix of bacteria and are also capable of releasing bacteria adhering to biological or inorganic material, as well as preventing their immediate reattachment. However, bacteria are not killed by trypsin treatment and, given time, will be able to recover their ability to attach to surfaces.

Thus, when administered individually, serine proteases or antibiotics are not able to completely resolve biofilm infections.

The present invention stems from the unexpected discovery of a synergistic effect upon bacterial biofilms when serine proteases (such as trypsins) and conventional antibiotic compounds are administered in combination. Surprisingly, this selected combination of active agents is able to destroy both the extracellular matrix and the bacteria within biofilms in a synergistic manner. Without wishing to be bound by theory, it is believed that by disrupting the extracellular matrix of biofilms, serine protease enable the antibiotics to penetrate deeper into the biofilm and access the bacterial cells that reside therein. This allows the antibiotic to exert its function on the bacteria, otherwise hampered by the barrier effects of the extracellular matrix.

It will be appreciated by persons skilled in the art that the combination therapies described herein may be used to kill, inhibit or prevent the growth of a microbial biofilm in any environment in which such biofilms may be found. Thus, biofilm may be associated with either an inert support or with a living support.

In one embodiment, the biofilm is associated with a living support. For example, the biofilm may grow or be susceptible to growth on a surface within the human or animal body.

Thus, the invention provides combination therapies as defined above for use in the treatment or prevention of a condition associated with the presence or growth of a biofilm.

For example, the combination therapies described herein may be used to treat or prevent a disorder or condition associated with the growth of a microbial biofilm at one of the following sited within the body:
(a) the respiratory tract (for example, recurrent bacterial infections of the upper and/or lower respiratory tract);
(b) the urinary tract (for example, cystitis);
(c) the sinuses (for example, chronic sinusitis);
(d) the ear (for example, middle ear infections);
(e) the heart (for example, endocarditis);
(f) the prostate (for example, chronic bacterial prostatitis);
(g) the bone (for example, osteomyelitis);
(h) the lungs (for example, infections in cystic fibrosis such as pneumonia);
(i) the kidneys (for example, infectious kidney stones and in peritoneal dialysis); and/or
(j) the skin.

In a further embodiment, the biofilm is associated with an inert support. Thus, the biofilm may grow or be susceptible to growth on the surface of a device implanted or otherwise inserted within the human or animal body.

For example, the combination therapies described herein may be used to treat or prevent an infection associated with the growth of a microbial biofilm on one of the following inert surfaces within the body:
(a) a catheter (for example, for intravascular or urinary tract use);
(b) a stent (for example, a coronary stent);
(c) a shunt (for example, a cerebrospinal shunt);
(d) an intubating or tracheotomy tube;
(e) an ophthalmic device (for example, contact lenses, scleral buckles and intraocular lenses);
(f) a joint prosthesis (i.e. arthroplasty and implantation of other orthopaedic devices).
(g) an artificial heart valve; and/or
(h) a breast implant.

Thus, it will be appreciated that the combination therapies as described herein are particularly suited to the treatment and prevention of nosocomial infections.

In one embodiment, the biofilm comprises or consists of Gram negative and/or Gram-positive bacteria.

Thus, the bacteria may be Gram positive bacteria, such as those selected from the group consisting of Staphylococci or Streptococci. For example, the bacteria may be Staphylococci, such as *Staphylococcus aureus* (e.g. methicillin-resistant *Staphylococcus aureus*, MRSA). Alternatively, the bacteria may be Streptococci, such as *Streptococcus mutans* and/or *Streptococcus sanguis*.

The bacteria may also be Gram negative bacteria, such as *Legionella*.

In one preferred embodiment, the biofilm comprises bacteria independently selected from the group consisting of *Streptococcus pneumoniae, Streptococcus mitis, Pseudomonas aeruginosa, Heamophilus influenza*, methicillin-resistant *Staphylococcus aureus*, methicillin-susceptible *Staphylococcus aureus, Streptococcus pyogenes, Streptococcus mutans, Streptococcus sanguinis, Legionella pneumophila, Clostridium difficile*, and any mixtures thereof.

Thus, said biofilm may comprise bacteria independently selected from *Streptococcus pneumonia, Streptococcus mitis, Pseudomonas aeruginosa* and *Heamophilus influenza*, or a mixture thereof.

For example, the biofilm may comprise or consist of Streptococci, such as *Streptococcus mitis* and/or *Streptococcus pneumoniae*.

The combination therapies of the invention will be administered to a subject in a pharmaceutically effective dose. A 'therapeutically effective amount', or 'effective amount', or 'therapeutically effective', as used herein, refers to that amount which provides a therapeutic effect for a given condition and administration regimen (for example, eradication, a reduction in size or retardation of growth of a bacterial biofilm). This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

A first, critical component of the combinations therapies of the invention is a polypeptide having serine protease activity.

By polypeptide having serine protease activity we include both naturally occurring and non-naturally occurring catalytic polypeptides capable of cleaving peptide bonds in proteins, in which serine serves as the nucleophilic amino acid at the active site of the polypeptide (as defined in accordance with EC Number 3.4.21). The serine protease activity may be chymotrypsin-like (i.e. trypsins, chymotrypsins and elastases) or subtilisin-like.

In one embodiment, the polypeptide having serine protease activity exhibits trypsin activity. For example, the polypeptide having serine protease activity may be a naturally-occurring trypsin, of either eukaryotic or prokaryotic origin, or a mutated version of such a trypsin. Specifically included are cold-adapted trypsins, such as a trypsin from Atlantic cod (*Gadus morhua*), Atlantic and Pacific salmon (e.g. Salmo salar and species of *Oncorhynchus*) and Alaskan Pollock (*Theragra chalcogramma*), and mutated forms thereof (as described below).

Three major isozymes of trypsin have been characterised from Atlantic cod, designated Trypsin I, II and III (see Ásgeirsson et al., 1989, *Eur. J. Biochem.* 180:85-94, the disclosures of which are incorporated herein by reference). For example, see GenBank Accession No. ACO90397.

In addition, Atlantic cod expresses two major isozymes of chymotrypsin, designated Chymotrypsin A and B (see Ásgeirsson & Bjarnason, 1991, *Comp. Biochem. Physiol. B* 998:327-335, the disclosures of which are incorporated herein by reference). For example, see GenBank Accession No. CAA55242.1.

In one embodiment, the polypeptide having serine protease activity comprises or consists of an amino acid sequence which shares at least 70% sequence identity with amino acid sequence of trypsin I from Atlantic cod (*Gadus morhua*), i.e. SEQ ID NO: 1:

[SEQ ID NO: 1]

16
|
IVGGYECTKHSQAHQVSLNSGYHFCGGSLVSKDWVVSAAHCYKSVLRVRLGEHHIRVNEG

79
|
TEQYISSSSVIRHPNYSSYNINNDIMLIKLTKPATLNQYVHAVALPTECAADATMCTVSG

141
|
WGNTMSSVADGDKLQCLSLPILSHADCANSYPGMITQSMFCAGYLEGGKDSCQGDSGGPV

200
|
VCNGVLQGVVSWGYGCAERDHPGVYAKVCVLSGWVRDTMANY (wherein the amino acid sequence and numbering is according to Protein Data Bank [PDB] entry '2EEK')

Like many proteases, trypsin I from Atlantic cod is produced as an inactive precursor, or zymogen, comprising a propeptide (or "activation") sequence that is cleaved off to generate the mature, active trypsin. The initial expression product for trypsin also comprises a signal sequence, which is removed following expression.

The zymogen sequence for trypsin I from Atlantic cod, including the signal sequence, is shown below as SEQ ID NO:2 (and corresponds to Uniprot database accession no. P16049-1):

[SEQ ID NO: 2]

```
         10         20         30         40         50
MKSLIFVLLL GAV*FAEEDK*I VGGYECTKHS QAHQVSLNSG YHFCGGSLVS 60         70         80         90        100
KDWVVSAAHC YKSVLRVRLG EHHIRVNEGT EQYISSSSVI RHPNYSSYNI
```

```
             110        120        130        140        150
        NNDIMLIKLT KPATLNQYVH AVALPTECAA DATMCTVSGW GNIMSSVADG 160        170        180        190        200
        DKLQCLSLPI LSHADCANSY PGMITQSMFC AGYLEGGKDS CQGDSGGPVV 210        220        230        240
        CNGVLQGVVS WGYGCAERDH PGVYAKVCVL SGWVRDTMAN Y
``` wherein:
Signal peptide=amino acids 1 to 13 (underlined)
Propeptide=amino acids 14 to 19 (bold italics)
Mature trypsin=amino acids 20 to 241

The term 'amino acid' as used herein includes the standard twenty genetically-encoded amino acids and their corresponding stereoisomers in the 'D' form (as compared to the natural 'L' form), omega-amino acids and other naturally-occurring amino acids, unconventional amino acids (e.g., α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the polypeptides shown, each encoded amino acid residue, where appropriate, is represented by a single letter designation, corresponding to the trivial name of the conventional amino acid.

In accordance with convention, the amino acid sequences disclosed herein are provided in the N-terminus to C-terminus direction.

Typically, the polypeptides used in the compositions of the invention comprise or consist of L-amino acids.

The polypeptide having serine protease activity may comprise or consist of an amino acid sequence which shares at least 80%, 85%, 90%, 95%, 95%, 97%, 98% or 99% sequence identity with SEQ ID NO:1.

Thus, in one embodiment, the polypeptide having serine protease activity may comprise or consist of the amino acid sequence of SEQ ID NO:1.

However, the polypeptide may alternatively comprise or consist of the amino acid sequence which is a mutant or variant of SEQ ID NO:1. By "variant" we mean that the polypeptide does not share 100% amino acid sequence identity with SEQ ID NO: 1, i.e. one or more amino acids of SEQ ID NO: 1 must be mutated. For example, the polypeptide may comprise or consist of an amino acid sequence with at least 50% identity to the amino acid sequence of SEQ ID NO: 1, more preferably at least 60%, 70% or 80% or 85% or 90% identity to said sequence, and most preferably at least 95%, 96%, 97%, 98% or 99% identity to said amino acid sequence. Thus, an amino acid at a specified position may be deleted, substituted or may be the site of an insertion/addition of one or more amino acids. It will be appreciated by persons skilled in the art that the substitutions may be conservative or non-conservative.

Percent identity can be determined by, for example, the LALIGN program (Huang and Miller, *Adv. Appl. Math.* (1991) 12:337-357, the disclosures of which are incorporated herein by reference) at the Expasy facility site: (http://www.ch.embnet.org/software/LALIGN_form.html) using as parameters the global alignment option, scoring matrix BLOSUM62, opening gap penalty −14, extending gap penalty −4. Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (as described in Thompson et al., 1994, *Nucl. Acid Res.* 22:4673-4680, which is incorporated herein by reference). The parameters used may be as follows:
Fast pair-wise alignment parameters: K-tuple(word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

Thus, the polypeptide having serine protease activity may be a variant of SEQ ID NO:1, such as those described in International Patent Application No. PCT/GB2015/051006 (Publication No. WO 2015/150799) to Enzymatica AB.

It will be appreciated by persons skilled in the art that the polypeptide having serine protease activity may alternatively comprise or consist of a fragment of any of the above defined amino acid sequences, wherein the fragment exhibits an antibacterial activity.

By "fragment" we include at least 5 contiguous amino acids of any of the above amino acid sequences, such as but not limited to SEQ ID NO: 1 or 2. For example, the fragment may comprise at least 10, 11, 12, 13, 14, 15, 16, 17, 18, 19, 20, 25, 30, 35, 40, 45, 50, 60, 70, 80, 90, 100, 120, 140, 160, 180, 200 or more contiguous amino acids of any of the above amino acid sequences.

Methods of identifying fragments of the above-defined serine protease polypeptides which retain an antimicrobial (i.e. antibacterial) activity are well known in the art. For example, a range of different fragments could be generated known recombinant methodologies, using the expression methods described in WO 2015/150799, and then exposed in vitro to representative microorganisms (such as bacterial strains, viruses and/or fungal strains) to determine which of the fragments inhibits (in part or in whole) the growth and/or proliferation of said microorganisms.

In one particularly preferred embodiment, the polypeptide having serine protease activity comprises or consists of the amino acid sequence of a naturally-occurring serine protease. Thus, the polypeptide having serine protease activity may consist of the amino acid sequence of a naturally-occurring trypsin, of either eukaryotic or prokaryotic origin. Specifically included are cold-adapted trypsins, such as a trypsin from Atlantic cod (*Gadus morhua*), Atlantic and Pacific salmon (e.g. *Salmo salar* and species of *Oncorhynchus*) and Alaskan Pollock (*Theragra chalcogramma*). For example, the polypeptide having serine protease activity may comprise or consist of the amino acid of SEQ ID NO:1.

Such naturally-occurring serine proteases may be purified from a source organism (e.g. Atlantic cod) or may be expressed recombinantly.

Thus, it will be appreciated by persons skilled in the art that such naturally-occurring serine protease polypeptides of the invention must be provided in a form different to that in which they are found in nature. For example, the polypeptide of the invention may consist of the amino acid sequence of a naturally-occurring eukaryotic trypsin but lack the glycosylation moieties present on the protein as it is expressed in nature.

The polypeptide component can be formulated at various concentrations, depending on the efficacy/toxicity of the serine protease being used. Preferably, the formulation comprises the active agent at a concentration of at least 0.001 µM, for example at least 0.01 µM, at least 0.1 µM, at least 1 µM, at least 10 µM, at least 100 µM, or at least 500 µM. Conveniently, the formulation comprises the active agent at a concentration of up to 1 mM, for example up to 500 µM, up to 100 µM, up to 10 µM, up to 1 µM, up to 0.1 µM, or up to 0.01 µM. In one embodiment, the serine protease polypeptide is present in the formulation at a concentration of between 0.001 and 10 µM. Thus, the therapeutic formulation may comprise an amount of a polypeptide sufficient to kill or slow the growth of bacteria in a biofilm population.

In one embodiment of this aspect, the activity of the serine protease polypeptide (e.g. cod trypsin) from 0.001 U/g to 32 U/g.

A further critical component of the combinations therapies of the invention is one or more antibiotic compounds.

Any known antibiotic compound may be utilised. For example, the one or more antibiotic compounds may be selected from the group consisting of amoxicillin, ampicillin, azithromycin, carbapenems, cefotaxime, ceftriaxone, cefuroxime, cephalosporins, chloramphenicol, ciprofloxacin, clindamycin, dalacin, dalfopristin, daptomycin, doxycycline, ertapenem, erythromycin, fluoroquinolones, meropenem, metronidazole, minocycline, moxifloxacin, nafcillin, oxacillin, penicillin, quinupristin, rifampin, sulfamethoxazole, teicoplanin, tetracycline, trimethoprim, vancomycin, bacitracin and polymyxin B, or a mixture thereof.

In one preferred embodiment, the one or more antibiotic compounds is/are selected from the group consisting of tetracycline, cefotaxime, vancomycin, erythromycin and oxacillin.

It will be appreciated by persons skilled in the art that the combinations therapies of the invention may comprise a single antibiotic compound or multiple antibiotic compounds.

The concentration of the antibiotics to be used in the combination therapies of the invention will depend on the particular antibiotic to be used and the indication and/or location of the biofilm to be treated, in accordance with common general knowledge in the field. Typically, the antibiotic will be formulated at a concentration of between 0.1 to 5% (by weight), for example between 0.1 to 1% (by weight).

A second, related aspect of the invention provides a polypeptide having serine protease activity for use in treating a bacterial biofilm in a subject, wherein the polypeptide is for use in combination with one or more antibiotic compounds.

A third, related aspect of the invention provides a polypeptide having serine protease activity in the preparation of a medicament for treating a bacterial biofilm in a subject, wherein the polypeptide is for use in combination with one or more antibiotic compounds.

Examples of suitable serine protease polypeptides and antibiotic compounds for use in relation to the second and third aspects of the invention are detailed above.

A fourth aspect of the invention provides a pharmaceutical composition comprising (a) a polypeptide having serine protease activity and (b) one or more antibiotic compounds, together with a pharmaceutically-acceptable buffer, excipient, diluent or carrier.

Examples of suitable serine protease polypeptides and antibiotic compounds for use in relation to the fourth aspect of the invention are detailed above.

In one embodiment, the polypeptide having serine protease activity is present in a concentration of at least 0.001 µM, for example at least 0.01 µM, at least 0.1 µM, at least 1 µM, at least 10 µM, at least 100 µM, or at least 500 µM. Conveniently, the composition comprises the active agent at a concentration of up to 1 mM, for example up to 500 µM, up to 100 µM, up to 10 µM, up to 1 µM, up to 0.1 µM, or up to 0.01 µM. In one embodiment, the serine protease polypeptide is present in the composition at a concentration of between 0.001 and 10 µM.

When trypsin obtainable from cod is used, its concentration in the compositions of the invention is from 0.001 U/g to 32 U/g (i.e. measured as activity units per gram of the final composition).

In one embodiment, the one or more antibiotic compounds is/are present in a concentration of from 0.1% to 5% by weight, for example 0.1% to 2%, 0.5% to 1.5%, and preferably 1%.

The pharmaceutical compositions may be prepared in a manner known in the art that is sufficiently storage stable and suitable for administration to humans and animals. For example, the therapeutic compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the trypsin activity of the polypeptide of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the peptide in the therapeutic preparation. The diluent may be one or more of saline, water, polyethylene glycol, propylene glycol, ethanol or oils (such as safflower oil, corn oil, peanut oil, cottonseed oil or sesame oil).

The "excipient" may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

In one embodiment, the polypeptide may be provided together with a stabiliser, such as calcium chloride.

Also, included in the compositions of the invention may be ultraviolet absorbants (e.g. N,N-dimethyl PABA octyl ester, octyl methyl cinnamate, butyl methoxydibenzoylmethane, di-p-methoxycinnamic acid-mono-2-ehyl hexanoic acid glyceryl, 2-hydroxy-4-methoxy benzophenone, 2-hydroxy-4-methoxy benzophenone-5-sodium sulfonate), lower alcohols (e.g. ethyl alcohol, isopropyl alcohol), preservatives (e.g. methyl paraben, ethyl paraben, propyl paraben, butyl paraben, phenoxy ethanol), bactericides (e.g. chlorohexidine, hydrochloride, trichlorocarbanilide, triclosan, zinc pyrithione), silver (e.g. elemental silver, silver oxide, silver nitrate, silver sulfadiazine, silver nanoparticles), coloring agents (e.g. dyes, pigments), flavoring agents (e.g. menthol, camphor, thymol, eucalyptol) powders, perfumes (e.g. essential oils, perfume of animal origin, synthetic pertume), vitamins (e.g. vitamin A and its derivatives, vitamin E and its derivatives, vitamin C and its derivatives, pantothenic acid, vitamin H, vitamin B and its derivatives), urea, water-soluble polymers (e.g. poly vinyl alcohol, polyvinyl pyrrolidone, carboxyl vinyl polymer, xanthan gum, hyaluronic acid), buffer agents (e.g. sodium glutamate, arginine, aspartic acid, citric acid, sodium citrate, lactic acid, sodium lactate), antibiotic, antifungal, antiviral and antiparasitic drugs.

The polypeptides having serine protease activity may be formulated into any type of therapeutic composition known in the art to be suitable for the delivery of polypeptide agents.

In one embodiment, the polypeptide and antibiotic compound(s) may simply be dissolved in water, saline, polyethylene glycol, propylene glycol, ethanol or oils (such as safflower oil, corn oil, peanut oil, cottonseed oil or sesame oil), tragacanth gum, and/or various buffers. For example, where the polypeptide is formulated to oral administration (such as in a mouth spray), the therapeutic composition may comprise the polypeptide dissolved in water, glycerol and menthol. An exemplary mouth spray formulation is marketed within Scandinavia as ColdZyme® (by Enzymatica AB, Lund, Sweden).

In a preferred embodiment, the invention provides a protease polypeptide and antibiotic compound(s) as described above in an osmotically active solution. For example, the polypeptide and antibiotic compound(s) may be formulated in glycerol or glycerine. Without wishing to be bound by theory, it is believed that such osmotically active solutions facilitate movement of fluid from within microbial cells to the extracellular milieu. This, in turn, is believed to facilitate the therapeutic effect of the polypeptides of the invention by creating a thin, active barrier that inhibits (at least, in part) the uptake of microbial cells such as bacteria and viruses by the host epithelial cells, e.g. of the oropharynx.

In a further embodiment, the therapeutic compositions of the invention may be in the form of a liposome, in which the polypeptide and antibiotic compound(s) are combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The therapeutic compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the therapeutic compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the peptide. The polymers may also comprise gelatin or collagen.

It will be appreciated that the therapeutic compositions of the invention may include ions and a defined pH for potentiation of action of the polypeptides. Additionally, the compositions may be subjected to conventional therapeutic operations such as sterilisation and/or may contain conventional adjuvants such as preservatives, stabilisers, wetting agents, emulsifiers, buffers, fillers, etc.

In one preferred embodiment, the therapeutic composition comprises the polypeptide and antibiotic compound(s) in a Tris or phosphate buffer, together with one or more of EDTA, xylitol, sorbitol, propylene glycol and glycerol.

The therapeutic compositions according to the invention may be administered via any suitable route known to those skilled in the art. Thus, possible routes of administration include inhalation, buccal, parenteral (intravenous, subcutaneous, intratechal and intramuscular), topical, ocular, nasal, pulmonar, parenteral, vaginal and rectal. Also administration from implants is possible.

In an alternative embodiment, the therapeutic compositions are administered parenterally, for example, intravenously, intracerebroventricularly, intraarticularly, intra-arterially, intraperitoneally, intrathecally, intraventricularly, intrasternally, intracranially, intramuscularly or subcutaneously, or they may be administered by infusion techniques.

They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Alternatively, the therapeutic compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Advantageously, the polypeptide is provided in a form suitable for delivery to the mucosa of the respiratory tract.

A fifth aspect of the invention provides a method for treating a solid tumour in a subject, the method comprising administering to the subject a therapeutically effect amount of (a) a polypeptide having serine protease activity and (b) one or more antibiotic compounds.

Examples of suitable serine protease polypeptides and antibiotic compounds for use in relation to the fifth aspect of the invention are detailed above.

By "treatment" we include both therapeutic and prophylactic use of the combined therapeutic agents. It will be appreciated by persons skilled in the art that the combination therapy may completely eradicate the bacterial biofilm or may provide a partial benefit (such as a reduction in the size of the bacterial population constituting the biofilm and/or slowing of growth of the bacterial population constituting the biofilm.

In one embodiment, the subject is human. However, the methods of the invention may also be useful in a veterinary setting, for example in the treatment of bacterial biofilms in domestic and/or farm animals (including dogs, cats, horses, cattle, pigs, sheep and the like).

It will be appreciated by persons skilled in the art that the methods described herein may be used to kill, inhibit or prevent the growth of a microbial biofilm in any environment in which such biofilms may be found. Thus, biofilm may be associated with either an inert support or a living support.

In one embodiment, the biofilm is associated with a living support (see above). For example, the biofilm may grow or be susceptible to growth on a surface within the human or animal body. Thus, the invention provides a compound as defined above for use in the treatment or prevention of a condition associated with the presence or growth of a biofilm. For example, the subject may have or be susceptible to an infection in the upper and/or lower respiratory tract associated with biofilm formation.

In a further embodiment, the biofilm is associated with an inert support (see above). Thus, the biofilm may grow or be susceptible to growth on the surface of a device implanted or otherwise inserted within the human or animal body.

Thus, it will be appreciated that the methods as described herein are particularly suited to the treatment and prevention of nosocomial infections.

In one embodiment, the biofilm comprises or consists of Gram negative and/or Gram-positive bacteria.

Thus, the bacteria may be Gram positive bacteria, such as those selected from the group consisting of Staphylococci or Streptococci. For example, the bacteria may be Staphylococci, such as *Staphylococcus aureus* (e.g. methicillin-resistant *Staphylococcus aureus*, MRSA). Alternatively, the bacteria may be Streptococci, such as *Streptococcus mutans* and/or *Streptococcus sanguis*.

The bacteria may also be Gram negative bacteria, such as *Legionella*.

In one preferred embodiment, the biofilm comprises bacteria independently selected from *Streptococcus pneumoniae, Streptococcus mitis, Pseudomonas aeruginosa, Heamophilus influenza*, methicillin-resistant *Staphylococcus aureus*, methicillin-susceptible *Staphylococcus aureus, Streptococcus pyogenes, Streptococcus mutans, Streptococcus sanguinis, Legionella pneumophila, Clostridium difficile*, and any mixtures thereof.

For example, the biofilm may comprise or consist of Streptococci, such as *Streptococcus mitis* and/or *Streptococcus pneumoniae*.

In the methods of the invention, the combination therapy will be administered to a patient in a pharmaceutically effective dose. A 'therapeutically effective amount', or 'effective amount', or 'therapeutically effective', as used herein, refers to that amount which provides a therapeutic effect for a given condition and administration regimen (see above).

A sixth aspect of the invention provides a medical device for delivery to a subject of an effective amount of a combination therapy according to the first aspect of the invention, the device comprising a reservoir of a composition according to the fourth aspect of the invention and means for releasing said composition from the device.

For example, the device may be a mouth spray or nasal spray suitable for delivering a combination therapy according to the first aspect of the invention to the mucosa of the respiratory tract.

In one embodiment, the invention provides an implantable medical device which is impregnated, coated or otherwise treated with a composition as described herein.

For example, the medical device is an implantable medical device selected from the group consisting of intravascular devices, catheters, shunts, intubating and tracheotomy tubes, ophthalmic devices, joint prostheses, artificial heart valves and breast implants. By "implantable device" we include devices attached an internal or external surface of the body, e.g. contact lenses.

Preferably, the implantable medical device is packaged in a sealed and sterile container prior to use A seventh aspect of the invention provides a method for killing, inhibiting or preventing the growth of a bacterial biofilm in vitro, the method comprising exposing the biofilm (or surface upon which biofilm growth is to be prevented) to a combination therapy according to the first aspect of the invention. For example, the above-described compositions of the invention may also be used in the form of a sterilising solution or wash to prevent the growth of microbial biofilms on a surface or substrate, such as in a domestic environment (e.g. kitchen work surfaces, showers, pipes, floors, etc.) or a commercial or industrial environment (e.g. within cooling systems, pipes, floor surfaces, etc.) environment.

Such wash solutions may further comprise a surface-active agent or surfactant. Suitable surfactants include anionic surfactants (e.g. an aliphatic sulphonate), ampho-teric and/or zwitterionic surfactants (e.g. derivatives of aliphatic quaternary ammonium, phosphonium and sulfo-nium compounds) and nonionic surfactants (e.g. aliphatic alcohols, acids, amides or alkyl phenols with alkylene oxides). Conveniently, the surface-active agent is present at a concentration of 0.5 to 5 weight percent.

In both in vitro and in vivo uses, the compositions of the invention are preferably exposed to the target surface for at least five minutes. For example, the exposure time may be at least 10 minutes, 20 minutes, 30 minutes, 40 minutes, 50 minutes, 1 hour, 2 hours, 3, hours, 5 hours, 12 hours and 24 hours.

The following drawing forms part of the present specification and is included to further demonstrate certain aspects of the present invention. The invention may be better understood by reference to this in combination with the detailed description of specific embodiments presented herein.

FIG. 1 Effects of combinations of cod trypsins with selected antibiotics on biofilm dispersal Effects of combination of cod trypsins with selected antibiotics on biofilm dispersal. The figure shows that the combination of cod trypsins and selected antibiotics can be more effective at disrupting biofilms than either alone. Biofilms using a combination of *Streptococcus pneumonia* and *Streptococcus mitis* were grown in a microtiter plate and used as a model for biofilm. The biofilm was treated with an antibiotic or a combination of the antibiotics and cod trypsins. The biofilms were stained with crystal violet followed by dissolution with acetic acid. Biofilm formation was measured as absorbance at 492 nm, and normalized to untreated biofilm. Based on the study it can be concluded that certain antibiotics, in this case tetracycline, erythromycin, oxacillin, and cefotaxime, and cod trypsin combinations are more effective in disrupting bacterial biofilm than antibiotics alone. However, vancomycin was shown not to have significantly increased efficacy against the model biofilm when combined with trypsin. P values above bars indicate significance of difference between the two treatments as evaluated by Student's t test.

Figure 2:
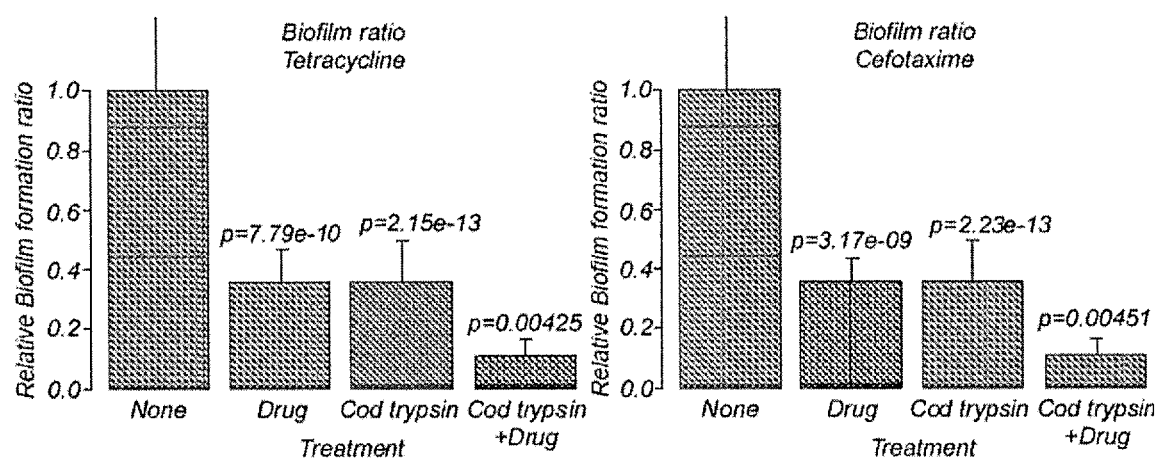

FIG. 2 Effects of combination of cod trypsins with selected antibiotics on biofilm dispersal.

Effects of combination of cod trypsins with selected antibiotics on biofilm dispersal. The figure shows that the combination of cod trypsins with tetracycline or cefotaxime can be more effective at disrupting biofilms than either alone. Biofilms using a combination of *Streptococcus pneumonia* and *Streptococcus mitis* were grown in a microtiter plate and used as a model biofilm. The biofilm was treated with cod trypsins, an antibiotic, or a combination of the two. The biofilms were stained with crystal violet followed by dissolution with acetic acid. Biofilm formation was measured as absorbance at 492 nm, and normalized to untreated biofilm. Based on the study it can be concluded that for this model combination of cod trypsin and the antibiotic tetracycline or cefotaxime are more effective in disrupting bacterial biofilm than either cod trypsins or antibiotics alone. P values above bars indicate significance of effects as evaluated by ANOVA analysis.

Figure 3:
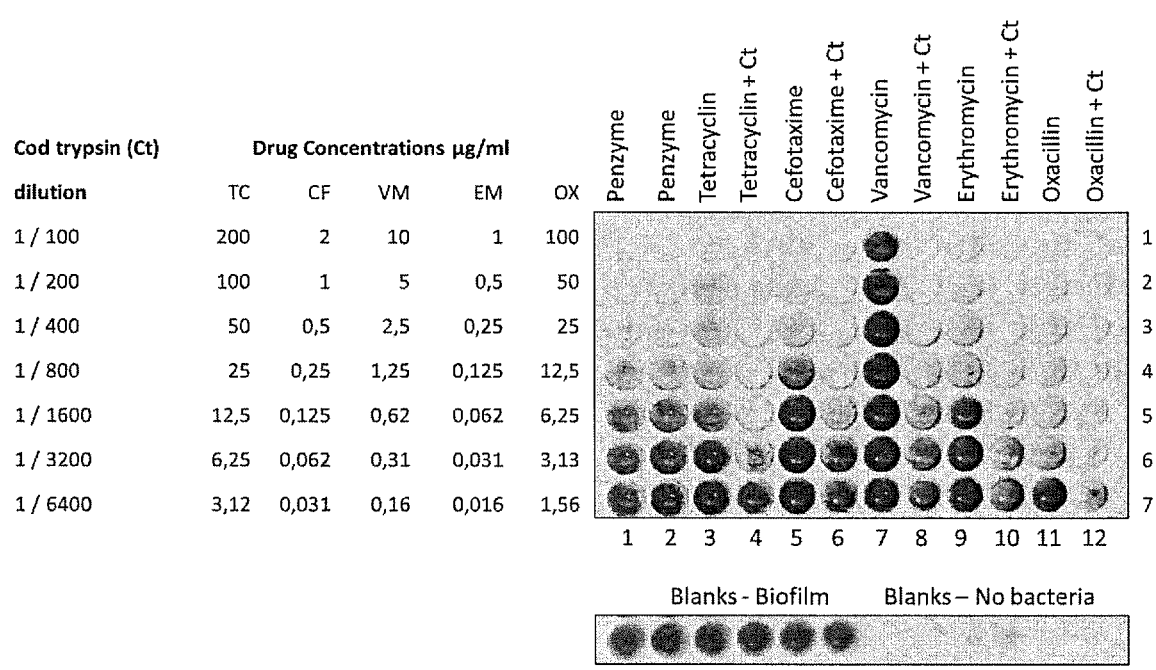

FIG. 3 Effects of combination of cod trypsins with selected antibiotics on biofilm dispersal Effects of combination of cod trypsins with selected antibiotics on biofilm dispersal. The image is a clear visual demonstration that the combination of cod trypsins and selected antibiotics can be more effective at disrupting biofilms than either alone. Biofilms using a combination of *Streptococcus pneumonia* and *Streptococcus mitis* were grown in a microtiter plate. The biofilm was treated with cod trypsins, an antibiotic, or a combination of the two. The biofilms were then stained with crystal violet. Based on the study it can be concluded that cod trypsins and antibiotic combinations are more effective in disrupting bacterial biofilm than antibiotics alone. As demonstrated by Vancomycin, the treatment of biofilms with antibiotics may increase biofilm formation, the effects of which are offset by presence of cod trypsin as evident by columns 7 and 8.

The image shows a 96 well plate where biofilms composed of *Streptococcus pneumonia* and *Streptococcus mitis* were grown for 4 hours followed by treatment with cod trypsin (ct), antibiotic, or cod trypsin/antibiotic combination. Each column represents one type of treatment or treatment combination, with the rows representing decreasing concentrations from top to bottom. After treatment biofilms are stained with crystal violet, with a darker colour representing more remaining biofilm. The image demonstrates that the combinations of antibiotics and cod trypsin can be more effective than either entity alone. This is especially profound for vancomycin where the drug alone appears to increase biofilm formation, while in combination with cod trypsin the vancomycin can increase the efficacy of cod trypsin. The lowest row represents blanks, where the first six holes represent untreated biofilm and the next six represent no biofilm. The table on the left side demonstrates the concentrations of cod trypsin and antibiotics used in each row/dilution.

The image demonstrates how trypsin increases the efficacy of certain antibiotics presumably by disrupting the biofilm and thereby granting the antibiotics access to the bacteria.

Figure 4:
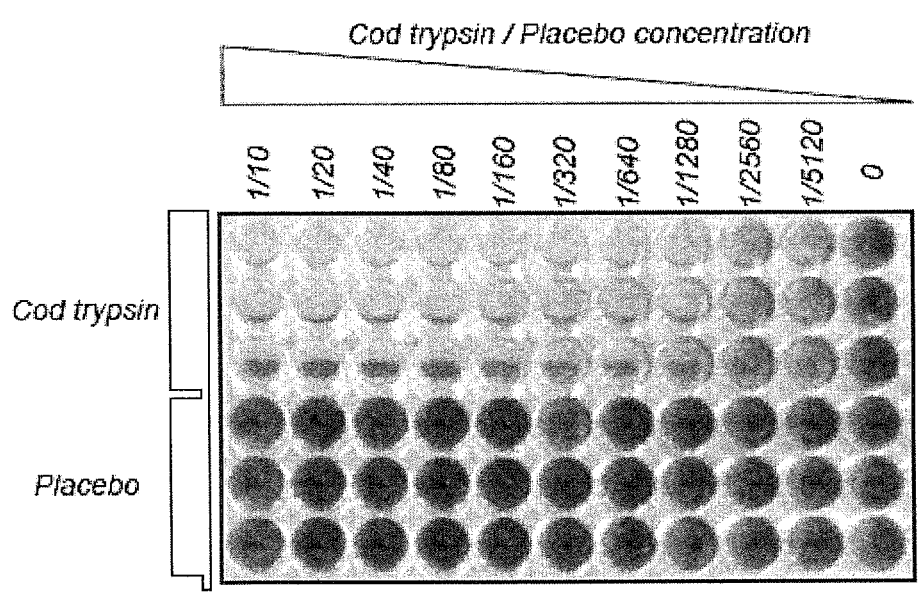

FIG. 4 Effects of cod trypsins on the super biofilm presented visually after biofilm staining with crystal violet.

Effects of cod trypsins on the super biofilm presented visually after biofilm staining with crystal violet. The figure shows that cod trypsins disrupt the super biofilm in a concentration dependent manner as seen by the clear wells indicating absence of biofilm. The super biofilm with a combination of *Streptococcus pneumonia* and *Streptococcus mitis* were grown in a microtiter plate. The biofilm was treated with cod trypsins or placebo for 2 minutes and the wells were stained to measure the presence (black wells) of biofilm or its absence (clear wells) after treatment. Based on the study it can be concluded that cod trypsins are very effective in disrupting the super biofilm.

The photographic image shows a 96 well plate where biofilms composed of *Streptococcus pneumonia* and *Streptococcus mitis* were grown for 4 hours followed by treatment with cod trypsin or placebo. Each column represents one concentration, with the first three rows representing replicates of cod trypsin treatment and the lower three rows show replicates of cod trypsin free formulation at the same dilution. After treatment the biofilms were stained with crystal violet, with a darker colour representing more remaining biofilm. The image demonstrates that cod trypsin can be effective at removing biofilms at the higher concentration but may require additional factors at the lower concentrations.

Figure 5:
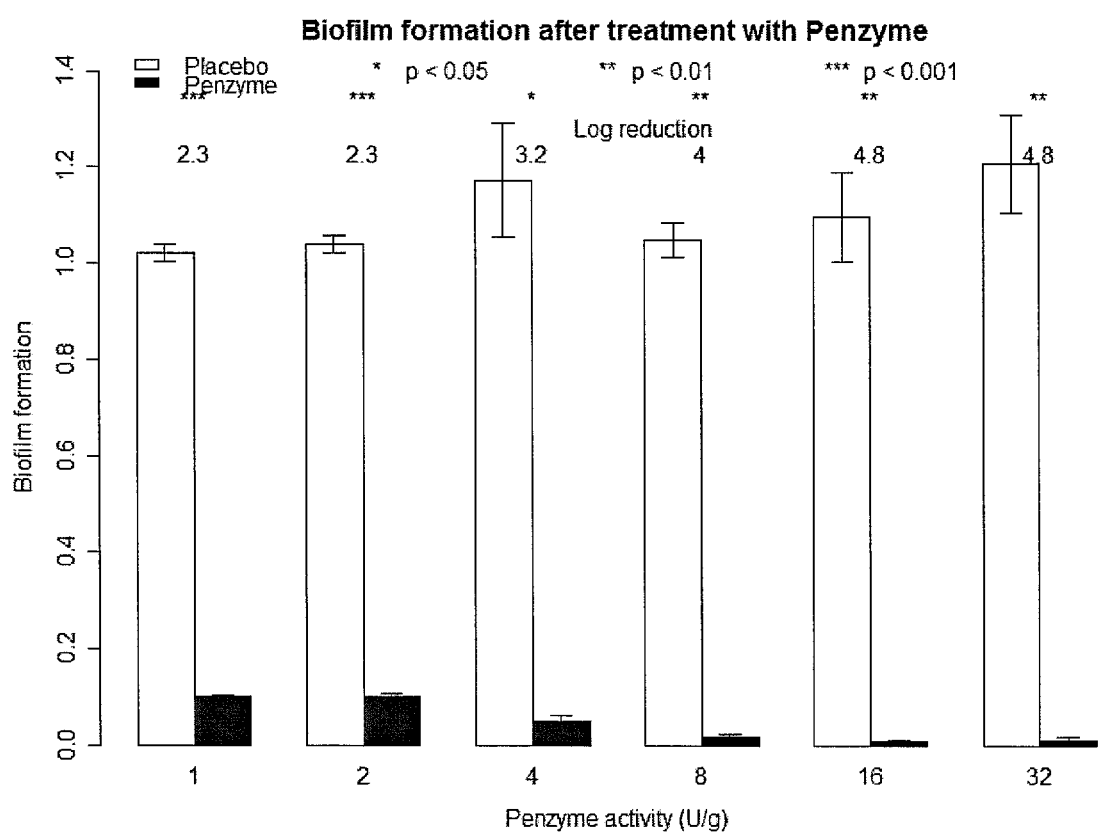

FIG. 5 Effects of cod trypsins on the super biofilm

Effects of cod trypsins on the super biofilm as measured by spectrophotometry after crystal violet staining and dissolution in acetic acid. The figure shows that cod trypsins disrupt the super biofilm in a concentration dependent manner. Biofilms using a combination of *Streptococcus pneumonia* and *Streptococcus mitis* were grown in a microtiter plate. The biofilm was treated with cod trypsins or placebo and the wells were stained with crystal violet followed by dissolution with acetic acid. Biofilm formation was measured as absorbance at 492 nm, and normalized to untreated biofilm. Based on the study it can be concluded that cod trypsins are very effective in disrupting bacterial biofilm. Data is presented as a bar-plot with the error bars indicating the standard error of the mean (SEM). Data for dilutions of placebo and cod trypsins treated bacterial biofilms are placed next to each other. The Log reduction of biofilm formation of Penzyme compared to that of placebo in the same dilution is above the bars, as is the level of significance indicated by asterisks (*), where * represents a P of <0.05,  a P<0.01 and * a P<0.001. Students T-test was used to calculate the significance.

Figure 6:
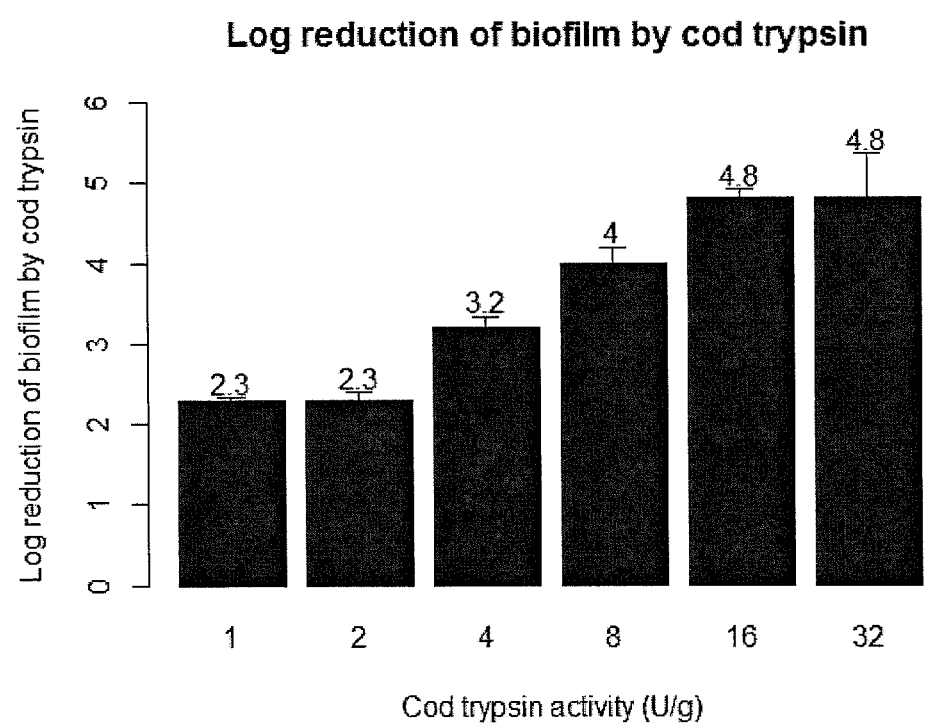

FIG. 6. Log reduction of super biofilm by cod trypsins at different concentrations.

Log reduction of super biofilm by cod trypsins at different concentrations. The figure shows that cod trypsins disrupt the super biofilm in a concentration dependent manner. Biofilms using a combination of *Streptococcus pneumonia* and *Streptococcus mitis* were grown in a microtiter plate. The biofilm was treated with cod trypsins or placebo and the wells were stained with crystal violet followed by dissolution with acetic acid. Biofilm formation was measured as absorbance at 492 nm, and the reduction compared to placebo treated biofilm on a logarithmic scale. Based on the study it can be concluded that cod trypsins are very effective in disrupting bacterial biofilm at concentrations 8 U/g or higher, in less than 2 minutes, where a log reduction of 3 represent 99.9% removal of the biofilm and a log reduction of 4 is 99.99% reduction of biofilm.

Figure 7:
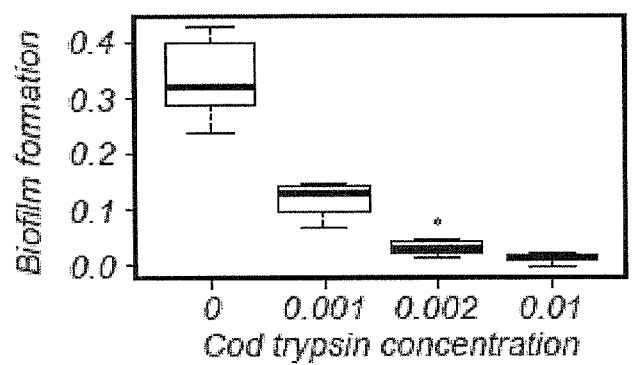

FIG. 7 Effects of cod trypsins pre-treatment on biofilm formation.

Effects of cod trypsins pre-treatment on biofilm formation. The figure shows that pre-treatment of the biofilm forming bacteria *Streptococcus pneumonia* and *Streptococcus mitis* with cod trypsin prior to incubation at 37° C. in a 96 well microtiter plate has a concentration dependent effect on their ability to form biofilms. Biofilms using a combination of *Streptococcus pneumonia* and *Streptococcus mitis* were grown in a microtiter plate after being briefly treated with cod trypsins or placebo. After allowing the biofilms to grow for 4 hours the wells were stained with crystal violet followed by dissolution with acetic acid. Biofilm formation was measured as absorbance at 492 nm, and normalized to untreated biofilm. Based on the study it can be concluded that cod trypsins are very effective in preventing bacterial biofilm formation. Data is presented as a boxplot where the top of the rectangle indicates the third quartile, a horizontal line near the middle of the rectangle indicates the median, and the bottom of the rectangle indicates the first quartile. A vertical line extends from the top of the rectangle to indicate the maximum value, and another vertical line extends from the bottom of the rectangle to indicate the minimum value.

Figure 8:
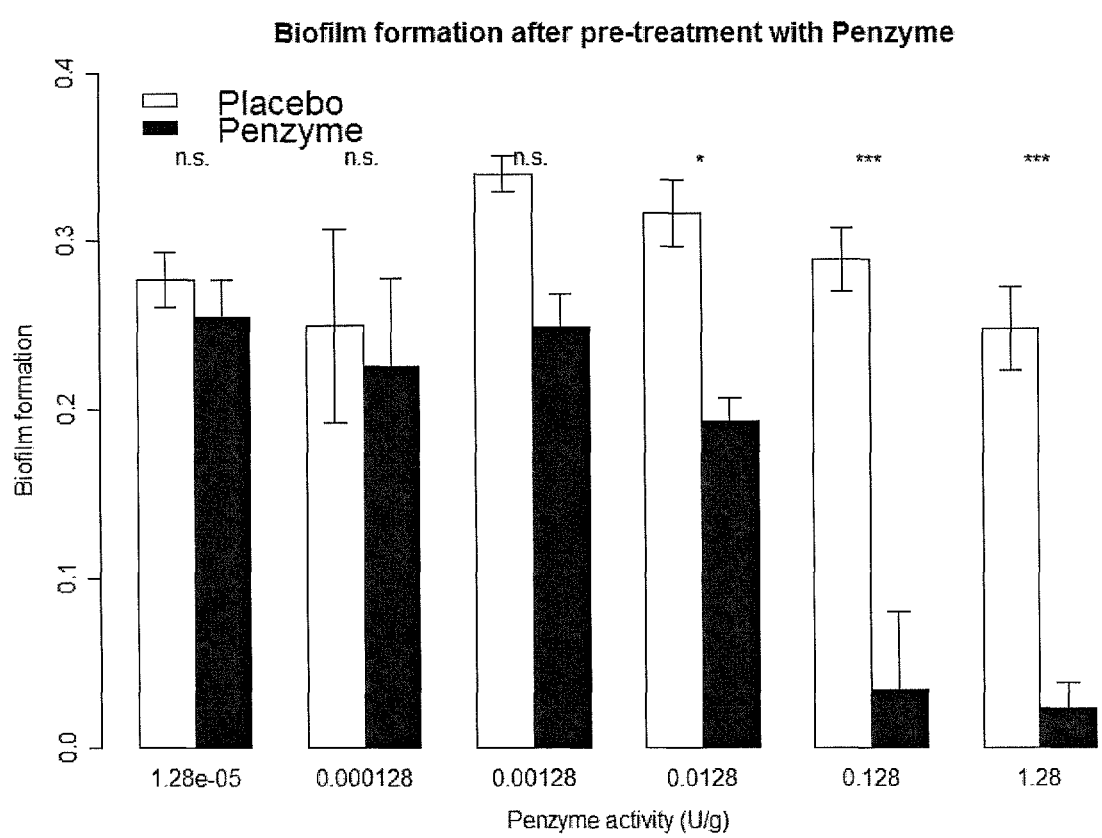

FIG. 8 Effects of cod trypsin pre-treatment on biofilm formation

Effects of cod trypsin pre-treatment on biofilm formation. The figure shows that cod trypsin can prevent the formation of biofilms in a concentration dependent manner when planktonic bacteria are treated with trypsin prior to being allowed to form biofilm. Biofilms using a combination of *Streptococcus pneumonia* and *Streptococcus mitis* were grown in a microtiter plate after being treated with cod trypsins or placebo. After allowing the biofilms to grow for 4 hours the wells were stained with crystal violet followed by dissolution with acetic acid. Biofilm formation was measured as absorbance at 492 nm, and normalized to untreated biofilm. Based on the study it can be concluded that cod trypsins are very effective in preventing bacterial biofilm formation. Statistical significance of the difference, as evaluated by Student's t test, is indicated by symbols above the boxes where n.s. is p >0.05, * is p<0.05,  p<0.01, and * p<0.001.

EXAMPLES

Example 1; Inhibition of Adhesion of Pneumococcus and *S. mitis* by a Cod Trypsin Composition As demonstrated in FIG. 1 and FIG. 2, biofilms using a combination of *Streptococcus pneumonia* and *Streptococcus mitis* were grown in a microtiter plate after being treated with cod trypsins or placebo. After allowing the biofilms to grow for 4 hours the wells were stained with crystal violet followed by dissolution with acetic acid. Biofilm formation was measured as absorbance at 492 nm, and normalized to untreated biofilm. Based on the study it is concluded that the cod trypsin composition was very effective in preventing bacterial biofilm formation. Treatment of bacteria with cod trypsin composition prior to biofilm formation showed a concentration dependent effect on biofilm formation in vitro. Cod trypsins prevent biofilm formation in a concentration dependent manner. Biofilms using a combination of *Streptococcus pneumonia* and *Streptococcus mitis* were grown in a microtiter plate after being treated with cod trypsins or placebo. After allowing the biofilms to grow for 4 hours the wells were stained with crystal violet followed by dissolution with acetic acid. Biofilm formation was measured as absorbance at 492 nm, and normalized to untreated biofilm. Based on the study it can be concluded that cod trypsins are very effective in preventing bacterial biofilm formation. Data is presented as a boxplot where the top of the rectangle indicates the third quartile, a horizontal line near the middle of the rectangle indicates the median, and the bottom of the rectangle indicates the first quartile. A vertical line extends from the top of the rectangle to indicate the maximum value, and another vertical line extends from the bottom of the rectangle to indicate the minimum value. Data for placebo and cod trypsin treated bacteria are placed on the same graph. Overlap of the boxes would indicate no difference in biofilm formation. Statistical significance of the difference, as evaluated by Student's t test, is indicated by symbols above the boxes where n.s. is p >0.05, * is p<0.05,  p<0.01, and * p<0.001. Results are presented in FIGS. 1 and 2.

FIGS. 4, 5, 6, 7, and 8 demonstrate that cod trypsins are quite capable of both removing bacteria from and partially prevent reattachment of bacteria to surfaces in a concentration dependent manner. This alone may however not be sufficient to completely eradicate bacterial infections as the cod trypsin is not lethal to the bacteria.

Example 2: Combination of Cod Trypsin and Antibiotics for Superior Biofilm Disruption by Such Trypsin Compositions Biofilms using a combination of *Streptococcus pneumonia* and *Streptococcus mitis* were grown in a microtiter plate. The biofilm was treated with an antibiotic or a combination of the antibiotics and cod trypsins. The biofilms were stained with crystal violet followed by dissolution with acetic acid. Biofilm formation was measured as absorbance at 492 nm, and normalized to untreated biofilm. It was concluded that cod trypsins and antibiotic combinations were more effective in disrupting bacterial biofilm than antibiotics alone (see FIG. 3). P values above bars indicate significance of difference between the two treatments as evaluated by Student's t test. Using selected antibiotics in combination with cod trypsins treatment showed that the use of cod trypsins significantly enhanced the effects of the antibiotics in 4 out of the 5 drugs tested as seen in FIG. 1. The data in FIG. 2 provide results where the biofilms were stained with crystal violet followed by dissolution with acetic acid. Biofilm formation was measured as absorbance at 492 nm, and normalized to untreated biofilm. P values above bars indicate significance of effects as evaluated by ANOVA analysis. The data demonstrate that the local combinatory use of cod trypsins with antibiotic treatment improved the disruption of biofilm compared to antibiotics alone. It was serendipitously discovered that a combination of cod trypsin with antibiotics improved the biofilm disruption by antibiotics. The addition cod trypsin allows the use of lower concentrations of antibiotics when treating biofilm infections. FIG. 3 shows effects of combination of cod trypsins with selected antibiotics on biofilm dispersal. The image is a clear visual demonstration that the combination of cod trypsins and selected antibiotics is more effective in disrupting biofilms than either alone. Biofilms using a combination of *Streptococcus pneumonia* and *Streptococcus mitis* were grown in a microtiter plate. The biofilm was treated with cod trypsins, an antibiotic, or a combination of the two. The biofilms were then stained with crystal violet. Based on the study it can be concluded that cod trypsins and antibiotic combinations are more effective in disrupting bacterial biofilm than antibiotics alone.

REFERENCES

Augustin, M., T. Ali-Vehmas, and F. Atroshi, 2004, Assessment of enzymatic cleaning agents and disinfectants against bacterial biofilms: Journal of Pharmacy and Pharmaceutical Sciences, v. 7, p. 55-64.

Bjarnason, J. B., 2000, Fish serine proteases and their pharmaceutical and cosmetic use. Patent: PCT, WO 00/78332 A2.

Gudmundsdottir, A., H. Hilmarsson, and B. Stefansson, 2013, Potential Use of Atlantic Cod Trypsin in Biomedicine: Biomed Research International.

Stefansson, B., L. Helgadottir, S. Olafsdottir, A. Gudmundsdottir, and J. B. Bjarnason, 2010, Characterization of cold-adapted Atlantic cod (*Gadus morhua*) trypsin I-Kinetic parameters, autolysis and thermal stability: Comparative Biochemistry and Physiology B-Biochemistry & Molecular Biology, v. 155, p. 186-194.

The invention claimed is:

1. A method for treating a bacterial biofilm in a subject, the method comprising administering to the subject a therapeutically effect amount of (a) a polypeptide having serine protease activity and (b) one or more antibiotic compounds, wherein the polypeptide having serine protease activity is Atlantic cod trypsin I having an amino acid sequence of SEQ ID NO: 1:

[SEQ ID NO: 1]
IVGGYECTKHSQAHQVSLNSGYHFCGGSLVSKDWVVSAAHCYKSVLRVRLG

EHHIRVNEGTEQYISSSSVIRHPNYSSYNINNDIMLIKLTKPATLNQYVHA

VALPTECAADATMCTVSGWGNTMSSVADGDKLQCLSLPILSHADCANSYPG

MITQSMFCAGYLEGGKDSCQGDSGGPVVCNGVLQGVVSWGYGCAERDHPGV

YAKVCVLSGWVRDTMANY.

2. A method according to claim 1, wherein the subject is human.

3. A method according to claim 1, wherein the biofilm is located in the upper and/or lower respiratory tract.

4. A method according to claim 1, wherein said biofilm comprises or consists of Gram negative and/or Gram-positive bacteria.

5. A method according to claim 1, wherein said biofilm comprises bacteria independently selected from *Streptococcus pneumoniae, Streptococcus mitis, Pseudomonas aeruginosa, Heamophilus influenza*, methicillin-resistant *Staphylococcus aureus*, methicillin-susceptible *Staphylococcus aureus, Streptococcus pyogenes, Streptococcus mutans, Streptococcus sanguinis, Legionella pneumophila, Clostridium difficile*, and any mixtures thereof.

6. A method according to claim 1, wherein said biofilm comprises *Streptococci*.

7. A method according to claim 1, wherein said biofilm comprises *Streptococcus mitis* and/or *Streptococcus pneumoniae*.

8. A method according to claim 1, wherein the polypeptide having serine protease activity is further administered as a mixture with chymotrypsin.

9. A method according to claim 1, wherein the one or more antibiotic compounds is a single antibiotic compound.

10. A method according to claim 1, wherein the polypeptide having serine protease activity is administered by mouth spray.

11. A method according to claim 1, wherein the Atlantic cod trypsin I has activity ranging from 0.1 to 16 U/g.

12. A method according to claim 1, wherein the polypeptide having serine protease activity comprises or consists of an amino acid sequence of SEQ ID NO: 1:

[SEQ ID NO: 1]
IVGGYECTKHSQAHQVSLNSGYHFCGGSLVSKDWVVSAAHCYKSVLRVRL

GEHHIRVNEGTEQYISSSSVIRHPNYSSYNINNDIMLIKLTKPATLNQYV

HAVALPTECAADATMCTVSGWGNTMSSVADGDKLQCLSLPILSHADCANS

YPGMITQSMFCAGYLEGGKDSCQGDSGGPVVCNGVLQGVVSWGYGCAERD

HPGVYAKVCVLSGWVRDTMANY.

13. A method according to claim 1, wherein the polypeptide having serine protease activity is purified from a natural source or is a recombinant protein.

14. A method according to claim 1, wherein the one or more antibiotic compounds is/are selected from the group consisting of amoxicillin, ampicillin, azithromycin, carbapenems, cefotaxime, ceftriaxone, cefuroxime, cephalosporins, chloramphenicol, ciprofloxacin, clindamycin, dalacin, dalfopristin, daptomycin, doxycycline, ertapenem, erythromycin, fluoroquinolones, meropenem, metronidazole, minocycline, moxifloxacin, nafcillin, oxacillin, penicillin, quinupristin, rifampin, sulfamethoxazole, teicoplanin, tetracycline, trimethoprim, vancomycin, bacitracin and polymyxin B, or a mixture thereof.

\* \* \* \* \*

UNITED STATES PATENT AND TRADEMARK OFFICE
CERTIFICATE OF CORRECTION

PATENT NO. : 11,338,021 B2
APPLICATION NO. : 15/746888
DATED : May 24, 2022
INVENTOR(S) : Agusta Gudmundsdottir and Reynir Scheving Page 1 of 1

It is certified that error appears in the above-identified patent and that said Letters Patent is hereby corrected as shown below:

In the Claims

In Claim 12, Column 24, Line 7, delete "comprises or".

Signed and Sealed this
Sixth Day of December, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 222
<212> TYPE: PRT
<213> ORGANISM: Gadus morhua

<400> SEQUENCE: 1

```
Ile Val Gly Gly Tyr Glu Cys Thr Lys His Ser Gln Ala His Gln Val
1               5                   10                  15

Ser Leu Asn Ser Gly Tyr His Phe Cys Gly Gly Ser Leu Val Ser Lys
            20                  25                  30

Asp Trp Val Val Ser Ala Ala His Cys Tyr Lys Ser Val Leu Arg Val
        35                  40                  45

Arg Leu Gly Glu His His Ile Arg Val Asn Glu Gly Thr Glu Gln Tyr
    50                  55                  60

Ile Ser Ser Ser Val Ile Arg His Pro Asn Tyr Ser Ser Tyr Asn
65                  70                  75                  80

Ile Asn Asn Asp Ile Met Leu Ile Lys Leu Thr Lys Pro Ala Thr Leu
                85                  90                  95

Asn Gln Tyr Val His Ala Val Ala Leu Pro Thr Glu Cys Ala Ala Asp
            100                 105                 110

Ala Thr Met Cys Thr Val Ser Gly Trp Gly Asn Thr Met Ser Ser Val
        115                 120                 125
```

```
Ala Asp Gly Asp Lys Leu Gln Cys Leu Ser Leu Pro Ile Leu Ser His
            130                 135                 140

Ala Asp Cys Ala Asn Ser Tyr Pro Gly Met Ile Thr Gln Ser Met Phe
145                 150                 155                 160

Cys Ala Gly Tyr Leu Glu Gly Gly Lys Asp Ser Cys Gln Gly Asp Ser
                165                 170                 175

Gly Gly Pro Val Val Cys Asn Gly Val Leu Gln Gly Val Val Ser Trp
            180                 185                 190

Gly Tyr Gly Cys Ala Glu Arg Asp His Pro Gly Val Tyr Ala Lys Val
        195                 200                 205

Cys Val Leu Ser Gly Trp Val Arg Asp Thr Met Ala Asn Tyr
    210                 215                 220

<210> SEQ ID NO 2
<211> LENGTH: 241
<212> TYPE: PRT
<213> ORGANISM: Gadus morhua

<400> SEQUENCE: 2

Met Lys Ser Leu Ile Phe Val Leu Leu Leu Gly Ala Val Phe Ala Glu
1               5                   10                  15

Glu Asp Lys Ile Val Gly Gly Tyr Glu Cys Thr Lys His Ser Gln Ala
            20                  25                  30

His Gln Val Ser Leu Asn Ser Gly Tyr His Phe Cys Gly Gly Ser Leu
        35                  40                  45

Val Ser Lys Asp Trp Val Val Ser Ala Ala His Cys Tyr Lys Ser Val
    50                  55                  60

Leu Arg Val Arg Leu Gly Glu His His Ile Arg Val Asn Glu Gly Thr
65                  70                  75                  80

Glu Gln Tyr Ile Ser Ser Ser Val Ile Arg His Pro Asn Tyr Ser
                85                  90                  95

Ser Tyr Asn Ile Asn Asn Asp Ile Met Leu Ile Lys Leu Thr Lys Pro
            100                 105                 110

Ala Thr Leu Asn Gln Tyr Val His Ala Val Ala Leu Pro Thr Glu Cys
        115                 120                 125

Ala Ala Asp Ala Thr Met Cys Thr Val Ser Gly Trp Gly Asn Thr Met
    130                 135                 140

Ser Ser Val Ala Asp Gly Asp Lys Leu Gln Cys Leu Ser Leu Pro Ile
145                 150                 155                 160

Leu Ser His Ala Asp Cys Ala Asn Ser Tyr Pro Gly Met Ile Thr Gln
                165                 170                 175

Ser Met Phe Cys Ala Gly Tyr Leu Glu Gly Gly Lys Asp Ser Cys Gln
            180                 185                 190

Gly Asp Ser Gly Gly Pro Val Val Cys Asn Gly Val Leu Gln Gly Val
        195                 200                 205

Val Ser Trp Gly Tyr Gly Cys Ala Glu Arg Asp His Pro Gly Val Tyr
    210                 215                 220

Ala Lys Val Cys Val Leu Ser Gly Trp Val Arg Asp Thr Met Ala Asn
225                 230                 235                 240

Tyr
```